United States Patent
Rajaraman

(12) 
(10) Patent No.: US 6,245,501 B1
(45) Date of Patent: *Jun. 12, 2001

(54) METHOD FOR CANCER SCREENING

(75) Inventor: Rengaswami Rajaraman, Hammonds Plains (CA)

(73) Assignee: Dalhousie University, Halifax (CA)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/759,295

(22) Filed: Dec. 2, 1996

(51) Int. Cl.$^7$ .............................. C12Q 1/00; A61K 9/44; G01N 1/30

(52) U.S. Cl. ..................... 435/4; 435/40.5; 435/40.51; 435/40.52

(58) Field of Search .................. 435/4, 40.5, 40.51, 435/40.52

(56) References Cited

PUBLICATIONS

Wyllie et al., Cell Death: The Significance of Apoptosis, Int. Rev. Cytol. 68:251 (1980).
Arends et al., Apoptosis: Mechanisms and Roles in Pathology, Int. Rev. Exp. Pathol. 32:223 (1991).
Ellis, Ronald et al., Mechanisms and Functions of Cell Death, Annu. Rev. Cell Biol. 7:663 (1991).
Raff, Martin C., Social Controls on Cell Survival and Cell Death, Nature 356:397 (1992).
White, Eileen, Life, Death and the Pursuit of Apoptosis, Genes Develop. 10:1 (1996).
Fisher, David E., Apoptosis in Cancer Therapy: Crossing the Threshold, Cell 78:539 (1994).
Martin, Seamus J., Protease Activation during Apoptosis: Death by a Thousand Cuts?, Cell 82:349 (1995).
Jacobson, Michael D., Programmed Cell Death and Bcl–2 Protection in the Absence of a Nucleus, EMBO J. 13(8):1899 (1994).
Schulze–Osthoff, Klaus et al., Cell Nucleus and DNA Fragmentation Are Not Required for Apoptosis, J. Cell Biol. 127:1 (1994).
Nakajima, H. et al., The Target Cell Nucleus is not Rquired for Cell–mediated Granzyme– or Fas–based Cytotoxicity, J. Exp. Med. 181:1905 (1995).
Caelles, C. et al., p–53–Dependent apoptosis in the absence of transcriptional activation of p53–target genes, Nature 370:220 (1994).
Rajaraman, R. et al., A Novel Form of Apoptosis without Cell Death and its Role in Neoplasia, Mol. Biol. Cell 6: Suppl. 519a 1996.
R. Rajaraman et al., Apoptosis without Cell Death, Mol. Biol. Cell 5:Suppl 342a (1995).
Gorczyca W. et al., Detection of DNA Strand Breaks in Individual Apoptotic Cells by the in Situ Terminal Deoxynucleotidyl Transferase and Nick Translation Assays, Cancer Res. 53:1945 (1993).
Maeda, S. et al., Cell Density–Dependent DNA Fragmentation and its Suppression by Heparin in Primary Culture of Adult Rat Hepatocytes, Biochem. Biophys. Res. Commun. 195:270 (1993).
Warren, G. et al., Membrane Partitioning During Cell Division, Annu. Rev. Biochem p. 323–48 (1993).
Berges, R. et al., Cell Proliferation, DNA Repair and p53 function are not required for programmed cell death of prostatic glandular cells induced by androgen ablation, Proc. Natl. Acad. Sci USA 90:8910 (1993).
Poumay, Y. et al., Cell Density and Culture Factors Regulate Keratinocyte Commitment to Differentiation and Expression of Suprabasal K1/K10 Keratins, J. Invest. Dermatol. 104:271 (1995).
Mathieu C. et al., Density–Dependent Induction of Apoptosis by Transforming Growth Factor–b1 in a Human Ovarian Carcinoma Cell Line, Exp. Cell Res. 216:13 (1995).
Rubin, H. et al., Heritable, population–wide damage to cells as the driving force of neoplastic transformation, Proc. Natl. Acad. Sci. USA 92:4843 (1995).
Rubin H. et al., Neoplastic development: Paradoxical relation between impaired cell growth at low population density and excessive growth at high density, Proc. Natl. Acad. Sci. USA 92:7734 (1995).
Rotheels K et al., Effects of X–Irradiated Feeder Layers on Mitotic Activity and Development of Aneudploidy in Mouse–Embryo Cells in vitro, Canadian Center Conference 5:191 (1962).
Sargent L. et al., Tamoxifen Induces Hepatic Aneuploidy and Mitotic Spindle Disruption after a Single in vivo Administration to Female Sprague–Dawley Rats, Cancer Res. 54:3357 (1994).
Traganos F. et al., Effect of Staurosporine on MOLT–4 Cell Progression Through G2 and on Cytokinesis, J. Cell Physiol. 158:535 (1994).
Tommerup N. et al., Chromosomal breakage, endomitosis, endoreduplication, and hypersensitivity toward radiomimetric and alkylating agents: a possible new autosomal recessive mutation in a girl with craniosynostosis and microcephaly, Hum Genet 92:339 (1993).
Hartwell L et al., Cell Cycle Control and Cancer, Science 266:1821 (1994).

(List continued on next page.)

*Primary Examiner*—Susan Ungar
(74) *Attorney, Agent, or Firm*—Harris F. Brotman

(57) ABSTRACT

Methods for detecting if a subject with tumor cells is at increased risk of developing tumor progression. The method involves determining the frequency of endoapoptosis in a sample of tumor tissue taken from the subject. The frequency of endoapoptosis in the tissue sample indicates whether the subject is at increased risk of developing tumor progression. Method for screening chemical agents for anti-tumor effects.

5 Claims, 2 Drawing Sheets

OTHER PUBLICATIONS

Dermer (Bio/Technology, 12:320), 1994.
Freshney (Culture of Animal Cells A Manual of Basic Technique, Alan R. Liss, NY, p. 4), 1983.
Gestblom et al (Eur. J. Can., 31A:458–463), 1995.
Masuda et al (J. Urol., 158:750–753), 1997.
Lipponen et al., Eur. J. Can., 30A:2068–2073), 1994.*
Tockman et al (Cancer Res., 52:2711s–2718s), 1992.*

* cited by examiner

METHOD FOR CANCER SCREENING

BACKGROUND OF THE INVENTION

1. Field of the Invention

The present invention relates to methods for studying tissue samples from a subject to predict the course of a tissue's tumor progression. In particular, the method determines the frequency of cells in a tissue which are undergoing abnormal cell division. More specifically, the invention relates to histochemical analysis of cell division in tissues.

2. Description of Related Art

The publications and other reference materials referred to herein to describe the background of the invention and to provide additional detail regarding its practice are hereby incorporated by reference. For convenience, the reference materials are numerically referenced and grouped in the appended bibliography.

Cells often kill themselves in a process known as apoptosis or programmed cell death. Apoptosis is necessary for the body to properly function. Apoptosis is essential during embryonic development, differentiation, tissue remodeling, maturation of the immune system, tumor regression, and viral infection and is also involved in homeostasis. Faulty regulation of apoptosis may lie behind many diseases.

Both external stimuli and internal stimuli can induce apoptosis. For example, addition of glucocorticoid hormones to immature thymocytes, withdrawal of interleukin-2 from mature thymocytes, the removal of colony stimulating factors from haematopoietic precursors, and lack of adhesion in normal cells, may trigger apoptosis. Internal stimuli such as irreparable damage to genomic DNA or toxicity may also induce apoptosis. Cells undergoing apoptosis show a sequence of characteristic morphological changes including membrane budding, cytoplasmic shrinkage, and the condensation and margination of chuomatin. Frequently, apoptosis is associated with the activation of an endonuclease(s) that degrades the genomic DNA into large or oligonucleosomal fragments to yield a characteristic DNA ladder upon gel electrophoresis. The dying cells are broken into membrane-bound apoptotic bodies, which are phagocytosed by neighboring cells, avoiding a possible inflammatory response due to leakage of cell contents [reviewed in 1–6].

Apoptosis is often called programmed cell death because several gene products are involved in the regulation and execution of this process. An understanding of the set of genes involved in apoptosis comes from the studies on the nematode *Caenorhabditis elegans* [5]. These genes may fall into two groups: those that regulate the cell death program, and those that are involved in the execution phase of apoptosis. The nematode gene, ced-9, encodes a protein homologous to the mammalian Bcl-2 family of cell death regulators [7, 8].

The Bcl-2 family of apoptosis regulatory proteins consists of pro- and anti-apoptotic genes. In addition, the tumor suppressor genes $p^{53}$ and Rb which are involved in cell cycle regulation are also involved in regulating apoptosis. Loss of their functions may confer resistance in tumor cells to apoptosis-inducing agents such as chemicals and ionizing radiations. Therefore, tumor cells are capable of surviving current therapeutic modalities, although the exact mechanism of tumor cell resistance to apoptosis-inducers is not well understood at present [9]. For prognosis, it is critically important to detect the earliest signs of tumor cells which have escaped anti-tumor therapy and are likely to progress toward neoplasia. Early detection methods are therefore needed.

The genes involved in the execution phase of apoptosis include the nematode gene, nuc-1, that encodes endonuclease required for DNA fragmentation, and ced-3, that encodes a cysteine protease with homology to interleukin-1β converting enzyme (ICE)[10]. Recent studies have identified a protease, yama/CPP32β, as a mammalian homolog of CED-3 [11]. Other ICE-like family of enzymes include Nedd-2/Ich-1, Tx/Ich-2, and Mch-2 [reviewed in 6, 12].

Recent studies have shown that the morphological events characteristic of apoptosis can be induced in cytoplasts in the absence of a nucleus [13, 14]. Similarly, the cell nucleus was not required for cell-mediated granzyme- or fas-induced cell death pathways in target cells [15]. These and other studies have lead to the hypothesis that the gene products required for apoptosis are constitutively expressed in the cytoplasm [13, 16].

Although resistance of tumor cells to apoptosis inducers (e.g. chemotherapeutic agents and radiation) has been widely observed, the morphological changes of cells that escape anti-tumor therapy induced apoptosis and progress towards malignancy are unknown. There is a need to morphologically characterize the earliest stages of cells which escape induced apoptosis in order to predict the progression of the tumor cells in the patient toward malignancy or neoplasia.

DISCLOSURE OF THE INVENTION

The present invention overcomes the problem of being unable to identity the mechanism and early stages of cells that escape genotoxin-induced apoptotis. The invention is based upon the discovery of a form of cell division herein referred to as "endoapoptosis," which represents the earliest known morphological changes characteristic of tumor cells which resist apoptosis induced by chemo-or radiation therapy. It will be understood that endoapoptosis can be considered a form of apoptosis but without resulting cell death. As a result of this discovery, the method of the invention predicts from the endoapoptotic appearance of tumor cells whether a tumor will progress toward malignancy.

The present invention provides a method of detecting if a subject with tumor cells is at increased risk of developing tumor progression. The method involves the step of determining the frequency of endoapoptosis in a sample of tumor tissue taken from the subject. The frequency of endoapoptosis in the tissue sample indicates whether the subject is at increased risk of developing tumor progression.

By determining the frequency of endoapoptosis in samples of tumor tissue obtained from a subject at various times either with or without treatment by chemicals and/or radiation, the invention further provides a method for monitoring the status of the tumor and the effectiveness of the treatment.

The above-discussed and many other features and attendant advantages of the present invention will become better understood by reference to the following detailed description of the invention taken in conjunction with the accompanying drawings.

MODES OF CARRYING OUT OF THE INVENTION

Figure 1:
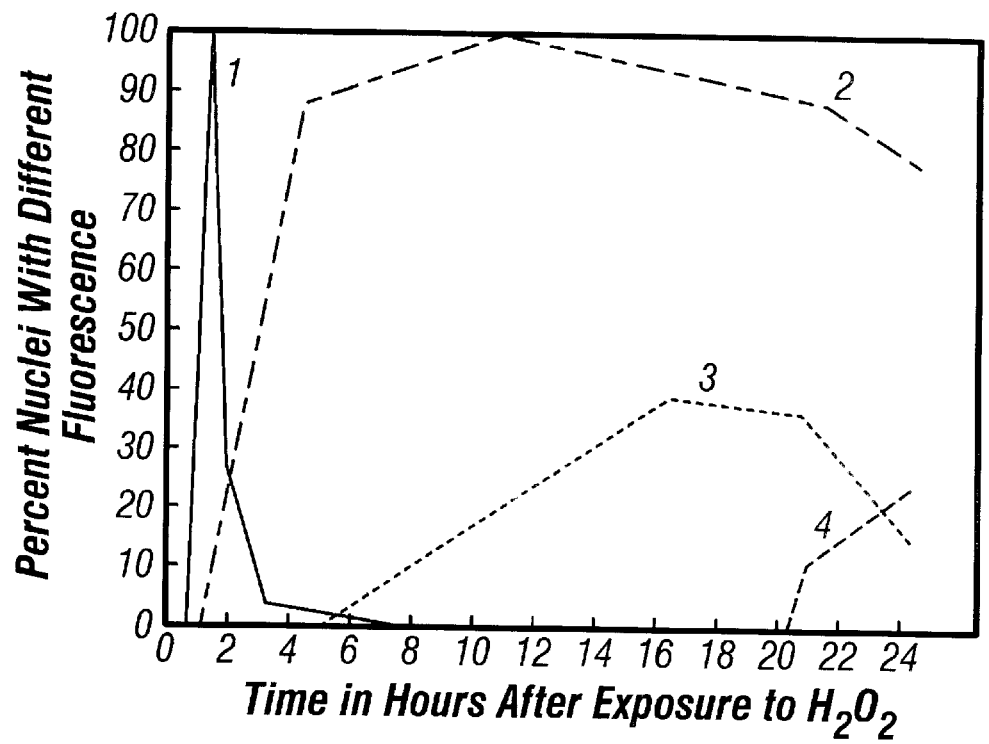
FIG. 1—Graphic representation of the temporal changes in the nuclear fluorescence pattern in A10 cells during classic apoptosis. A10 cells were stained with acridine orange at different times after exposure to hydrogen peroxide (0.2 mM) and at least 500 cells were scored at each time interval to obtain the above graph. Lines 1–4 represent the frequency of apoptotic nuclei having characteristic fluorescence patterns. A concentration of 0.1 mM hydrogen peroxide induced similar changes with a 24 h delay.

Certain advantages are provided by the method of the present invention for characterizing normal, preneoplastic or neoplastic status of an abnormal tissue growth, including the tissue's genomic instability, in terms of the frequency of endoapoptosis in such tissues. These advantages include providing more reliable prognostic and diagnostic criteria in evaluating the stage of tumor progression in a subject than are currently available.

General Description and Definitions

The practice of the present invention will employ, unless otherwise indicated, conventional cell culture, histochemistry, biochemistry, irradiation of cell cultures, light and electron microscopy, within the skill of the art. Such techniques are explained fully in the literature. See, e.g. *Methods in Enzymology,* Vol. LVIII, Cell Culture, ed. W. B. Jakoby and I. H. Pastan, Academic Press, NY (1979); *Tissue Culture Methods and Applications,* Kruse, P. F. Jr., and Patterson, M. K., Academic Press, (1973); *Cell Biology, A Laboratory Manual,* ed. Celis, J. E., Academic Press, NY; *Histochemistry,* Pearse, A. G. E., Vol. 1 (1980), Vol. 2 (1985), and vol. 3 (1990); *Phase Constrast and Interference Microscopy,* Ross, K. F. A., Edward Arnold Publ. Ltd, London (1967); *Optical Microscopy, Emerging Methods and Applications,* Herman, B., and Demasters, J. J., Academic Press (1993); *Practical Methods in Electron Microscopy,* Vol. 1–9, North-Holland Pub. Co., Amsterdam, NY; Meyn, r. E. and Withers, H. R., *Radiation Biology and Cancer.* The Univ. of Texas System Cancer Center M.D. Anderson Hospital and Tumor Institute, 32 Annual Symposium on Fundamental Cancer Research, Raven Press, NY.

The following terminology will be used in accordance with the definitions set out below in describing the present invention.

The term "genomic instability," as used herein, indicates a high degree of tolerance in tumor cells for genomic infidelity, which would otherwise induce apoptotic death in normal cells. Genomic instability confers a proliferative advantage to tumor cells under adverse growth conditions. In normal cells, genomic integrity is stably maintained so that the number of chromosomes (and the DNA therein) is faithfully replicated and passed on to the daughter cells during each mitotic division. Checkpoint control by the tumor suppressor gene p53 ensures the orderly progression of cell cycle events through G1, G2 and M phases of the cell cycle (66–69). p53, being a transcription factor, modulates the expression of different genes involved in apoptosis, cell cycle progression, and DNA repair synthesis among others. Changes in genomic material, such as the appearance of extra chromosomes or extra set of chromosomes (I.e. ploidy changes) are seen when normal cells undergo neoplastic transformation spontaneously or due to other causes, including exposure to radiation, and chemicals, at times in the form of anti-tumor therapy, or exposure to viruses. Inactivation of p53 function by mutations or by otherwise compromising wild type p53 function results in loss of checkpoint controls, which favors genomic instability and increases the rate of acquisition of genomic alterations leading to genomic heterogeneity in neoplastic cells.

The term "genotoxin" refers to an anti-tumor agent such as irradiation or chemicals which damages DNA.

The term "apoptosis," as described in detail above in "Description of Related Art," refers to a process in which cells kill themselves. As observed under a microscope, the changes that such cells undergo are described herein. Apoptosis is also referred to below as "classical apoptosis."

"Neoplasia" or new growth usually means an abnormal growth of tissue, which eventually may turn into malignant tumor.

"Malignancy" and "metastatic disease" are used in the context of tumor cells which can be benign or malignant. A benign tumor grows slowly, has limited growth, and does not destroy normal cells. A benign tumor continues to grow in the place where it originated, and consists of differentiated cels. Unless it grows in a confined space, a benign tumor does not have serious side effects. Benign tumors may often regress and disappear completely. The primary tumor may become malignant in that it can become invasive locally, destroying adjacent normal tissues or by becoming metastatic, releasing tumor cells into the lymphatics and blood vessels. Tumor cells released into the circulation may lodge in different parts of the body and give rise to secondary metastatic tumors. The malignant tumor, which is composed of undifferentiated cells, grows rapidly, destroys normal cells, has suited growth potential, and is life threatening. The term "metastatis" can also be used for the cancer that has spread. For example, a patient might have a breast metastasis in the lung. Metastasis or metastatic tumor is often referred to as a "secondary tumor."

"Tumor Progression." A tumor is an abnormal tissue growth or mass on or in the body that serves no useful purpose. A tumor can be benign (noncancerous, usually in the early stages of tumor progression) or malignant (cancerous, usually in the advanced states of tumor progression), Tumor progression refers to the evolutionary origin of a given tumor. A normal cell must undergo several gene mutations before it becomes progressively tumorigenic. These mutations could be due to gain of function mutations in protooncogenes, or due to loss of function mutations in the tumor suppressor genes. Repeated mutations of different genes in the same cell result in the uncontrolled growth of a tumor cell. In vivo, this multistep carcinogenesis might take several years and this process is termed tumor progression or development. A normal cell may go through several stages (mutations) before it becomes a full fledged malignant cells, such as a preneoplastic stage followed by accumulation of mutations in multiple genes, finally leading to a malignant situation.

The term "tumor burden" usually refers to the mass of tumor tissue carried by a subject.

An "abnormal tissue growth" may or may not be tumorigenic, but it is usually a cause for concern. Abnormal cell division in a tissue may give rise to hyperplasia (overgrowth), metaplasia (growth of normally differentiated cells in the wrong place), or neoplasia (new abnormal growth that is tumorous).

The term "clonogenic" refers to a cell when it gives rise to a clone or colony of cells by continuous proliferation. The tumor cells are usually highly clonogenic since they have unlimited division potential.

The invention is based on the discovery of endoapoptosis (as defined below) in tumor cells. As observed, endoapoptosis was an early detectable morphological event of tumor cells which escaped from radiation- or chemo-therapy induced apoptosis. The endoapoptotic cells progressed into, i.e. survived to multiply and give rise to clones of neoplastic cells. Accordingly, as observed herein, the method of the invention determined that the relative frequency of apoptosis went down during tumor progression, and the frequency of endoapoptosis went up, allowing the method of the invention to find utility in distinguishing benign, relatively benign or slow growing tumors from their expansionist and potentially lethal counterparts. In particular, the methods of the invention are directed to:

Detecting if a subject with tumor cells is at increased risk of developing tumor progression;

Detecting malignancy of tumor tissue;

Monitoring the status of a tumor in a subject over time;

Determining the clinical stage of a cancer;

Screening one or more tissues from a subject for the presence of malignant cells;

Screening for the presence of metastatic disease in a biological sample; and

Screening for the presence of genomic instability in a biological sample.

It will be understood that the term "subject" refers to mammals, and, in particular to humans; and that the term "biological sample" refers to tissue from a mammal, or, in particular, a human.

The following example is offered by way of illustration and is not intended to limit the invention in any manner.

EXAMPLE 1

Discovery and Characterization of Endoapoptosis
1. Bi- and Multinucleate Cells in Normal, Preneoplastic and Neoplastic Cell Lines Multinucleate cells in various normal, preneoplastic, and neoplastic cells lines were carefullly examined, photographed and drawn under light and electron microscopy. Materials and methods employed were as follows:

Cells: Rat smooth muscle cell line A10, mouse embryo fibroblast line NIH3T3, and the human tumor cell lines HeLa cells (epithelioid carcinoma of the cervix), ACHN (renal adenocarcinoma), HTB11 (SK-N-SH, neuroblastoma, metastasis to bone), HT1080 (fibrosarcoma) cells, breast cancer cell lines BT20 and MCF-7 were obtained from American type culture collection. Primary cultures of mouse embryo fibroblasts (MEF) was initiated from 10 day old BalbC mouse embryos (Jackson Laboratories). Human foreskin cells were kind gifts of Dr. S. H. S. Lee (Dalhousie University). All cells were cultured in Dulbecco's modified Eagle's medium containing 10% fetal calf serum or new born calf serum (Gibco/BRL), and supplemented with 100 units/ml penicillin G sodium, 100 µg/ml streptomycin sulfate and 0.25 µg/ml amphotericin-B, in a humidified water jacketed incubator at 37.5° C. with 8% $CO^2$.

In situ end labeling with terminal deoxytransferase (TDT labeling): In situ end labeling with terminal deoxytransferase [18] was performed using ApopTag kit (Oncor) as recommended by the supplier. Following incorporation of digoxigenin-dUTP at 3'-OH ends of DNA breaks with terminal deoxytransferase, cells were reacted with peroxidase conjugated anti-digoxigenin antibody. Immobilized peroxidase produced a brown insoluble precipitate in the presence of the substrate diaminobenzidine. Control cells processed without terminal deoxytransferase did not yield brown precipitate (not shown).

Acridine orange and DAPI staining: Cells grown on glass coverslips were stained for 3–4 minutes in 100 µg/ml acridine orange (Sigma Chemicals Ltd) dissolved in HBSS; coverslips were rinsed briefly in HBSS and mounted in HBSS [19]. Cells were examined immediately in a Zeiss Axioskop fluorescence microscope equipped with filter #9 and epi-illumination. Double stranded DNA fluoresces green while single-stranded RNA and DNA fluoresce red after staining with acridine orange. In most of the experiments, endoapoptosis was scored by the presence of the endoapoptotic nuclei (mini cells) in very early (bright green fluorescence), mid phase (red fluorescence), late phase (no specific fluorescence) or the presence of a 'ghost' with no nuclear matrix, with or without fragmentation of the mini cells.

Cells were fixed for ten minutes in neutral formalin and stained with 1 µg/ml of 4',6'-diamidino-2-phenylindole (DAPI) [20] dissolved in HBSS for 10 mins and examined in fluorescence microscope with filter#2. DNA fluoresces blue under these conditions. Photographs were taken using Kodak Ektachrome Elite 100 ISA film.

Irradiation and fusion of cells: Human normal diploid foreskin fibroblasts (passage 20) cultured in 10 cm petri plates were irradiated with 10 Gy units at the rate of 3.5 cGy/s with Siemens X-ray unit and were harvested 1 h after irradiation for fusion with unirradiated human foreskin cells from sister culture. Cell fusion was achieved by mixing the irradiated or unirradiated cells with unirradiated human foreskin cells and exposing the cell pellet to 1 ml of 50% (v/v) polyethylene glycol (MW 6000) (Fisher Scientific) in distilled deionized water for 90 minutes and then washing off polyethylene glycol with gradual addition of Hank's balance salt solution (HBSS) at the rates of 3 ml/l minute, 5 ml/30 seconds and 17 ml for 30 s respectively. The washed cells were seeded on glass cover slips in standard growth medium and the cells were allowed to a attach and spread for 8 hours. The cover slips were scored for bi- and multinucleate cells with and without endoapoptotic bodies after staining with acridine orange.

Reproductive viability of the surviving nucleus in multinucleate endoapoptotic cells: Cells cultured in 20 µM 5-BUdR for 2 h were processed for immunofluorescence microscopy as described [21]. Monoclonal anti-5-BUdR Clone BU-33 (Sigma Chemicals) and FITC-anti-mouse-IgG (Cappel Laboratories) were used to detect nuclei in various phases of mitosis in cells displaying residual endoapoptotic bodies.

Electron microscopy: For studying endoapoptosis in transformed foci NIH3T3 cells were grown on Thermanox plastic coverslips and the cells were processed as monolayer by fixation with 2% glutaraldehyde in 0.1 M cacodylate buffer, pH 7.3, overnight at 5° C., and post-fixed with 1% osmium tetroxide acid. Cells were in block stained overnight in 0.5% aqueous uranyl acetate, dehydrated in acetone and embedded in Epon resin. Thin sections were cut, stained with uranyl acetate and lead citrate and viewed in a Philips 300 electron microscope. In some cases the monolayer of cells were scraped with rubber policeman after fixation and pelleted and processed for sectioning as above.

Clonogenicity of radiation-induced multinucleate endoapoptotic cells: Cells were exposed to X-radiation (10 GY) using a Siemens Orthovoltage X-ray Machine, model #5310941S3535, at the rate of 3.46 cGy/s. In order to investigate the temporal relationship between DNA synthesis, endoapoptosis, and the viability of radiation-induced multinucleate endoapoptotic cells, HeLa cells seeded on glass coverslips (5,000 cells/cm$^2$) were irradiated (X-radiation, 10 Gy) and were labeled with 5-bromoxeodyuridine (BUdR) for 3 h at different post-irradiation time (3, 6, and 12 hours post-irradiation (PIH), and 1, 2, 3, 4, 5, 7, and 9 days post-irradiation (PID), and processed for immunofluorescence as described [21]. The cells synthesizing DNA and the origin of multinucleate cells through post-irradiation day 10 were quantitated. These cells were observed for developing into multi nucleate giant cells and for clonal growth through several days. In some experiments, four days after exposure to X-radiation, HeLa cells were harvested and 500 and 1000 cells were seeded/10 cm petri plate with grids in duplicate. Individual multinucleate cells were observed every 6–12 hours up to ten post-irradiation days and the clonal outgrowth of mononucleate cells from multinucleate giant cells were recorded by line drawings. In addition, colony forming ability of multinucleate endoapoptotic giant cells was studied by plating irradiated HeLa cells (5, 10, and 15 Gy X-radiation) on post-irradiation day 4, in 10 cm petriplates in duplicate at the rate of 250, 500, and 1000 cells/plate in 20% new born calf serum containing DMEM+25% conditioned medium; the medium was changed twice a week and the number of colonies counted at the end of four weeks after irradiation. A sample of surviving colonies were isolated and grown by subculturing for observing long term survival.

Results

1. Demise of one or more nascent daughter cells in multinucleate cells

A careful examination of bi and multinucleate cells in various normal, preneoplastic and neoplastic cell lines in light microscopy with and without acridine orange or DAPI staining revealed that these cells displayed intracellular endoapoptotic body consisting of a nucleus and a small amount of cytoplasm (mini cell) in various stages of spontaneous apoptosis-like disintegration As shown in Table 1, a total of 500 cells were scored on the basis of residual endoapoptotic body and the nuclear ghosts. The frequency of multinucleate endoapoptotic cells (MuNEA+), multinucleate cells without endoapoptotic nuclei (MuNEA−), mononucleate cells with one or more endoapoptotic body (MoNEA+), mononucleate cells with no endoapoptotic body (MoNEA−) and total frequency of both multi- and mononucleate endoapoptotic cell frequency (Total EA+) were expressed as percentage. BI, before irradiation; PDI, post-irradiation (10 Gy X-radiation) day 5.

TABLE 1

Frequency of Multi Nucleate Endoapoptotic Cells in Different Cell Types Studied

| Cell type: | | MuNEA+ | MuNEA− | MoNEA+ | MoNEA− | Total EA+ |
| --- | --- | --- | --- | --- | --- | --- |
| Hfs (p.15) | UI | 0.0 | 0.0 | 1.0 | 99.0 | 7.0 |
| MRC-5 (p.48) | UI | 2.5 | 2.5 | 18.5 | 76.0 | 21.0 |
| MEF (p.15) | UI | 1.5 | 1.0 | 8.5 | 89.0 | 10.0 |
| NIH3T3 | UI | 1.0 | 2.5 | 10.5 | 86.5 | 11.5 |
|  | PID 5 | 1.5 | 4.0 | 2.5 | 92.0 | 4.0 |
| MCF-7 | UI | 5.0 | 52.0 | 6.0 | 42.0 | 11.0 |
| BT20* | UI | 6.0 | 3.0 | 56.0 | 35.0 | 62.0 |
|  | PID5 | 19.5 | 11.0 | 52.5 | 17.0 | 72.0 |
| ACHN | UI | 3.0 | 2.5 | 38.0 | 56.5 | 41.0 |
|  | PDI 5 | 6.5 | 2.0 | 36.5 | 54.5 | 45.5 |
| HTB11** | UI | 1.0 | 19.0 | 3.0 | 78.0 | 4.0 |
|  | PID 5 | 6.5 | 3.0 | 32.5 | 58.0 | 39.0 |
| HT1080*** | UI | 5.5 | 1.5 | 31.0 | 62.5 | 36.5 |
|  | PID 5 | 20.0 | 45.0 | 9.0 | 16.5 | 39.0 |
| HeLa | UI | 2.0 | 1.0 | 3.0 | 94.0 | 5.0 |
|  | PID 5 | 18.0 | 70.0 | 3.0 | 9.0 | 21.0 |

*BT20 cells show essentially non-fragmented large nuclear ghosts for a long time, which is then broken down into small vesicles.
**HTB11 cells form bi or multi nucleate giant cells which exocytose the endoapoptotic mini cell rapidly.
***HT1080 cells mainly form giant cells which show residual nuclear ghosts, indicating the endoapoptotic nuclei have been dismantled rapidly leaving their ghosts.

Acridine orange staining revealed variation in the nuclear fluorescence under ultraviolet light ranging from light green and bright green to red fluorescence and to lack of specific fluorescence. Chromatin in normal healthy nuclei fluoresced green. Chromatin margination and condensation (compaction of DNA) in the early-stage of nuclear disintegration was indicated by bright green fluorescence. Some endoapoptotic nuclei fluoresced red, while others fluoresced yellow or showed no specific fluorescence. When fragmentation of the endoapoptotic mini cells occurred, the multiple fragments displayed a similar variation in the fluorescence pattern, indicating that the fragmented nuclei went through similar disintegrative changes.

In the final stages of endoapoptosis, the contents of the endoapoptotic bodies were completely broken down leaving a vacuole-like mini cell 'ghost', whether the dying mini cell fragmented or not, that showed neither green nor red fluorescence, with or without residual nuclear matrix. Staining with acridine orange as well as with DAPI revealed the absence of DNA in these 'ghosts' as indicated by the absence of green or blue fluorescence, respectively. Thus, the disintegration of the mini cell with its nuclear DNA and the nuclear matrix left a large membrane-bound 'ghost' or several smaller vesicular 'ghosts' after the fragmentation of the endoapoptotic body indicating that this was once a multi nucleate cell. The preneoplastic and neoplastic cells showed varying frequency of endoapoptotic cells, while the normal diploid cells showed a background frequency of 1–2% endoapoptosis (Table 1). Thus endoapoptosis was of common occurrence in preneoplastic cells and occurred in a higher frequency in neoplastic cells.

To compare the postmortem changes in the nuclear fluorescence pattern during endoapoptosis with similar changes during classic apoptosis, classic apoptosis was induced in A10 cells with 0.02 mM hydrogen peroxide in the culture medium [23] and the temporal events were followed over 24 hours. A negligible number of cells underwent the classical apoptosis and detachment, with typical fragmented nuclei [1]. A majority of the cells, however, did not complete this process; instead the cells died before they became detached from the substratum and their nuclei displayed temporal changes in fluorescence as shown in FIG. 1. The highly condensed apoptotic nuclei fluoresced bright green compared to the non-condensed chromatin of normal cells. About 2–3 hours after $H_2O_2$-induced apoptotic death, these nuclei displayed red fluorescence, indicating the postmortem changes in the nucleus [22]. The red fluorescence was only partially sensitive to RNAse A digestion suggesting that the red fluorescence was probably due to a change in the pH [24] and persisted for about 3–6 hours, after which the nuclei gradually lost red fluorescence, turned yellowish, and finally displayed no specific fluorescence (FIG. 1). Thus, the progressive disintegration of the chromatin and the nuclear matrix followed similar fate both during endoapoptosis and during the classical apoptosis (FIG. 1).

To further confirm the similarities between endoapoptosis and classical apoptosis, A10 cells grown on coverslips were used to study DNA fragmentation in bi- and multi nucleate cells using terminal deoxytransferase mediated in situ end labeling technique (TdT labeling), which gives a brown precipitate as an indication of DNA fragmentation [18]. This study revealed DNA fragmentation in 60–80% of multi nucleate cells. Faint brown precipitate in an otherwise normal nuclei (without any apparent sign of chromatin condensation) indicated the early stages of DNA fragmentation, which often occurred in a progressive fashion. In later stages, the endoapoptotic nuclei exhibited advanced DNA fragmentation (rich brown precipitate), chromatin/nuclear matrix condensation, and shrinkage of the endoapoptotic body resulting in its withdrawal from the boundary of the endoapoptotic body. In in situ endlabelled preparations the cytoplasmic domain of the endoapoptotic body was not visible, and was probably masked by the brown precipitate. Dismantling of the mini cell gave rise to one large, residual 'mini cell ghost' or the dying mini cell was fragmented giving rise to residual smaller 'ghosts'. Diffuse brown precipitate was often observed in the living domain of the cytoplasm, suggesting that broken down DNA may be recycled. Thus, the results obtained with in situ end labeling, acridine orange and DAPI staining procedures demonstrated that important characteristics of classic apoptotic cell death such as DNA fragmentation, cytoplasmic shrinkage, chromatin marginization and condensation followed by fragmentation of the dying cell [18, 22, 25, 26] also characterized endoapoptosis.

2. High cell density induced endoapoptosis and transformed foci in preneoplastic cells. A10 cells in semi confluent cultures showed a frequency of 10–15% bi and multi nucleate cells on the basis of morphological integrity of the nuclei. However, when the residual endoapoptotic bodies in mononucleate cells were taken into consideration, 30% of the cells were multinucleate. When A10 cells reached confluence, the percent of cells displaying endoapoptosis increased dramatically to 70–80% of the population. Since high cell density is known to induce spontaneous neoplastic transformation in preneoplastic cells, it was of importance to find out if endoapoptosis was involved in the spontaneous formation of transformed foci. This was studied by culturing NIH3T3 mouse fibroblasts and A10 rat smooth muscle cells on glass cover slips for several weeks with change of medium twice a week. Early passage primary Hfsk cells (passage 15), late passage primary human MRC-5 cells (passage 50) and mouse embryonic fibroblasts (passage 15) were used as controls. The endoapoptotic bodies in various stages of disintegration as recognized by acridine orange stain or the presence of nuclear ghosts were used to identify the cells undergoing endoapoptosis. A10 cells, as observed earlier, under subconfluent conditions displayed 10–15% endoapoptotic cells; under confluent conditions, the frequency of endoapoptotic cells reached almost 100%, often with cells showing several endoapoptotic nuclei in different stages of disintegration. When the cells were maintained under confluence for several weeks, transformed foci were formed on these confluent monolayers of cells showing endoapoptosis as indicated by smaller cells piling upon each other. The cells in the transformed foci also showed a high frequency of endoapoptosis, as indicated by the margination/condensation of chromatin resulting in bright green fluorescence as opposed to dark green fluorescence in healthy nuclei. However, not all cells in the high cell density monolayer gave rise to transformed foci simultaneously. In NIH3T3 cells, no widespread endoapoptosis was evident when cells were subconfluent. When the cells began to overlap during transformed focus formation, a high frequency of cells in the focus displayed the phenomenon of endoapoptosis. The frequency of endoapoptotic cells and the frequency of focus formation was higher and the duration of confluence required for transformed foci formation was shorter in A10 cells, compared to NIH3T3 cells. This was consistent with A10 cells being were further progressed towards transformation than NIH3T3 cells. In contrast, late passage human primary fibroblasts, MRC-5 and mouse embryonic fibroblasts showed 2–4% endoapoptosis as indicated by nuclear ghosts (Table 1) and there was no density dependent increase in the frequency of endoapoptosis within the period of observation (8 weeks).

The incidence of endoapoptosis in tumor cells was studied using different cell lines. All these cells showed varying degree of endoapoptosis even under subconfluent culture conditions, as shown in Table 1. In high cell density areas, the human renal adenocarcinoma derived ACHN tumor cells also produced secondary 'transformed' foci (reminiscent of multi step carcinogenesis), which was preceded by endoapoptotic cells; this secondary focus formation was copious and very rapid and occurred within 3–5 days as opposed to several weeks in preneoplastic A10 and NIH3T3 cells. Usually the multinucleate endoapoptotic cells were much larger than the mononucleate cells. The human metastatic neuroblastoma derived HTB11 cell and the human fibrosarcoma derived HT1080 cells displayed high percentages of giant and multi nucleate endoapoptotic cells irrespective of cell density. On the other hand, HeLa cells showed only 2–6% endoapoptosis.

3. Transmission electron microscope of cells in transformed foci undergoing endoapoptosis While the transformed foci stained with acridine orange did show endoapoptotic and healthy nuclei in the same cells, phase contrast microscopy of the same field was not helpful to demonstrate the co-existence of the dying and healthy nuclei in the same cell, since the cells were overlapping. Therefore, electron microscopy was used to study the fine structure of the endoapoptotic body using the high cell density-induced transformed foci in NIH3T3 cells, that showed a high frequency of endoapoptotic cells.

Electron microscopy confirmed the presence of the dying and the living nucleus in the same cell and that the endoapoptotic nucleus was in fact a dying mini cell with a nucleus surrounded by cytoplasm. In the early stages of endoapoptosis, a double membrane was in the process of being assembled, compartmentalizing the nascent dying mini daughter cell from the living domains of the mother cell; the nucleus showed signs of apoptosis in that the chromatin marginization had already occurred. The nuclear envelope was dismantled leaving no membrane boundary between the nucleus and the cytoplasm within the dying mini cell. In later phases of endoapoptosis, the double membrane formed during compartmentalization by asymmetric intracellular cytokinesis separated from each other, probably due to the linkage of the dying mini cell, and the condensed chromatin was broken down leaving a fibrillo-granular nuclear matrix, which also eventually disappeared leaving a mini cell ghost, that may or may not be fragmented. Similar structures were seen in the transformed foci of A10 cells also.

Transmission electron microscopy of hydrogen peroxide-induced apoptotic cells on the other hand showed typical apoptotic changes in the nucleus such as chromatin marginization and condensation as has been described in other cell systems previously [2]. The nuclei in the cell undergoing apoptosis were surrounded by the nuclear envelope with no cytoplasmic inclusions within the nuclear envelope, which, at a later stage, could be dismantled. This indicated that endoapoptosis shared several properties of the nuclear changes seen in classic apoptosis such as DNA fragmentation, chromatin marginization and condensation, and fragmentation and dissolution of the nuclear envelope matrix.

The compartmentalization of the endoapoptotic body by a double membrane appeared homologous to cytokinesis that follows karyokinesis during mitosis [27], a process which is known to be facilitated by microfilaments [27]. Accordingly, when this was tested with fluoresceine isothiocyanate conjugated phalloidin, a majority of the endoapoptotic bodies (85%) were surrounded by microfilaments both before and during fragmentation. In electron micrographs, the microfilament bundles were also seen around the double membrane that compartmentalized the endoapoptotic mini cell. Thus, abortive cell division resulted due to the nascent mini cell committing post-mitotic suicide, accompanied by compartmentalization of the dying endoapoptotic body by asymmetric intracellular cytokinesis delimiting the living fraction of the cytoplasm of the same cell containing a viable daughter nucleus.

4. Viability of the surviving nucleus in an endoapoptotic cell

In most multinucleate cells, while the non-viable mini cell committed suicide by endoapoptosis, there was no visible evidence of apoptotic changes in the surviving nucleus or the rest of the cytoplasm, indicating that there was no total cell death. Because of the possibility that the healthy nuclei in such cells might also eventually die resulting in total cell death., it was deemed important to find out if the surviving nucleus was capable of division or it would also be eventually eliminated resulting in total cell death. Hence, the mitogenic potential of the viable nucleus within the cell displaying endoapoptosis was studied in A10 cells by pulse (3 h) chase (12–24 h) studies with the thymidine analog 5-bromodeoxyuridine (BUdR) followed by immunofluorescence detection of the incorporated BUdR.

During the short pulse period the healthy nuclei entered S phase in about 30–40% of the cells with endoapoptotic bodies. These cells then entered mitosis and successfully completed telophase around 12–24 hours. This indicated that these cells were viable and were capable of successfully completing mitosis. As in the case of classical apoptosis [28], the nuclear fragments in the endoapoptotic bodies also displayed repair DNA synthesis. The reproductive viability of endoapoptotic cells was also confirmed by acridine orange staining of live cells with endoapoptotic bodies undergoing mitotic division. Some cells with endoapoptotic bodies also underwent endomitosis.

5. The multinucleate state was not sufficient to induce endoapoptosis

To test if bi- or multinucleate condition itself and not the chromosomal abnormalities due to karyotype instability induced endoapoptosis, primary (diploid) human foreskin fibroblastic cells (Hfsk) were fused with unirradiated or X-irradiated (8 Gy) Hfsk fibroblasts and the frequencies of endoapoptotic cells were scored after acridine orange staining (Table 2).

TABLE 2

Frequency of Endoapoptosis in Fusion Products Between Normal and Normal, Normal and Irradiated (8 Gy) Primary Hfsk Cells (pass 16) Mixed in 1:1 and 1:2 Ratios. EA+ With Endoapoptosis; EA−, Without Endoapoptosis.

| | No. nuclei/cell | | | | | | |
|---|---|---|---|---|---|---|---|
| | MunEA− | | | MuNEA+ | | | |
| Treatment of cells | 2 | 3 | 4 | 2 | 3 | 4 | %MuNEA+ |
| Normal diploid human cells X with normal human diploid cells | 84 | 9 | 4 | 3 | 0 | 0 | 3 |
| Normal diploid human cells X irradiated normal human diploid cells (1:1) | 44 | 8 | 2 | 42 | 4 | 0 | 46 |
| Normal diploid human cells X irradiated normal human diploid cells (1:2) | 27 | 6 | 5 | 59 | 2 | 1 | 62 |

Fusion among unirradiated populations yielded 3% endoapoptotic multi nucleate cells. However, the frequencies of multi nucleate cells with endoapoptotic bodies were much higher in fusion experiments with irradiated cells with increasing fraction of irradiated cells as fusion partners. These studies indicated that chromosomal damage caused by irradiation and not the multinucleate state were the stimulus for the induction of endoapoptosis.

6. Ionizing radiation induced endoapoptosis in neoplastic cells

The above experiments indicated that chromosomal anomalies incurred during anaphase in aneuploid cells due to genomic instability might have triggered endoapoptosis in the nascent daughter cells. To confirm that a disturbance in karyotype equilibrium might enhance the frequency of endoapoptosis, different cell lines were irradiated with 10 Gy units of X-radiation and the changes in the frequency of endoapoptosis recorded (Table 1). Irradiated tumor cells generally displayed a higher frequency of multi nucleate cells and endoapoptosis around 3–6 days post irradiation (Table 2). However, NIH3T3 cells that display density dependent inhibition of cell division, did not show any dramatic increase in the frequency of endoapoptosis or of multinucleate cells within this time. In ACHN and HeLa cells, radiation-induced multinucleate giant cells displayed endoapoptosis. The giant cells formed by irradiated HT1080 and HTB11 cells did not show more than one or two endoapoptotic nuclei at a given time. HT1080 giant cells showed residual fragmented nuclear ghosts, indicating that the endoapoptotic bodies had been rapidly fragmented and disintegrated without being accumulated in the cytoplasm. Time lapse observations showed that the dismantling of the dying mini cell was completed within 1 hr, leaving a mini cell ghost that persisted for several hours. The giant cells in HTB11 cell line, on the other hand, exocytosed the endoapoptotic mini cells rapidly, which were often found attached to the giant cell surface. 18 extruded endoapoptotic mini cells attached to one giant cell were counted. These purged dead mini cells were in advanced stages of DNA disintegration, most showing complete disintegration of chromatin as seen after DAPI staining. In these populations, the frequency of multinucleate cells would be highly underestimated, due to lack of residual endoapoptotic bodies in the cytoplasm.

7. Clonogenicity of irradiation-induced multi nucleate endoapoptic cells

At different times after irradiation, HeLa cells were examined with DAPI stain for DNA and were examined for microscopic evidence of cell damage. The cells were quantitated for DNA synthesis by BUdR incorporation, and the origin of multinucleate cells through post-irradiation day 10 were quantitated.

Within 12 hours after irradiation, the cells were fill of dilated cytoplasmic lacunae, including the ballooning of the membranes of the nuclear envelope. These radiation-induced immediate pathological changes were reversible in most surviving cells by day 4–5. Roughly about 20% of the cells were undergoing classical apoptosis at a given time by total cell death every day up to post-irradiation day 5. These cells were probably damaged irreversibly.

Figure 2:
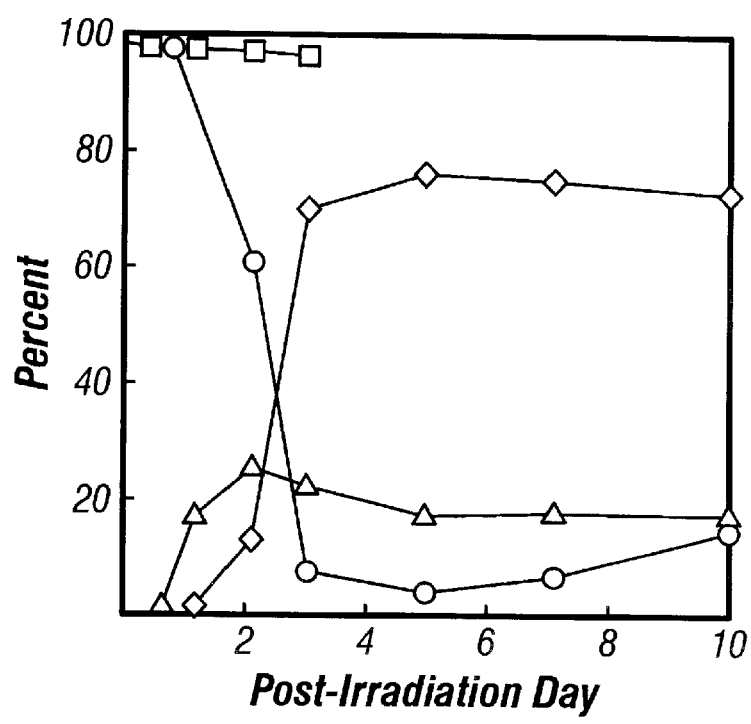
FIG. 2—Temporal sequence of the origin of multi nucleate endoapoptotic HeLa cells after exposure to X-irradiation (10 Gy). Note that the decline in mononucleate cells starting from day 1, is followed by increase in bi nucleate cells; the frequency of binucleate cells declines as the multi nucleate giant cells, of which about 20–25% display endoapoptosis at a given time, are formed due to continuous DNA synthesis and karyokinesis in the absence of cytokinesis, by post-irradiation day 3. (See also Table no. 6). Mononucleate cells begin to increase in number by day 6–10. Closed squares, Frequency of mono nucleate cells in unirradiated control; closed circles, the frequency of mono nucleate cells in irradiated HeLa cells; closed triangles, the frequency of binucleate cells; closed diamonds, the frequency of multi nucleate cells.

The changes in DNA synthesis due to irradiation and the kinetics of the origin of multi nucleate cells are shown in Table 3 and FIG. 2. Unirradiated HeLa cells showed almost 100% of the cells incorporating BUdR with a mitotic frequency of 2–3% during the course of three days (observed duration). After irradiation, about 50% of the mononuclear cells were synthesizing DNA as indicated by BuDr incorporation at 3–6 h post-irradiation. The frequency of cells synthesizing DNA reached the lowest level by 12 h. There was a gradual reduction in mononuclear cells from almost 100% on day 0 to about 6% by post-irradiation day 5. This was accompanied by a peak increase in bi nucleate cells by post-irradiation day 2 and an increase in the frequency of multi (more than two) nucleate giant cells by day 5–7. During this period of continuous DNA synthesis and origin of multinucleate giant cells, mitotic cells were conspicuous by their absence in the irradiated population of cells, indicating that nuclear division was achieved by endomitosis and endoreduplication accompanied by suppression of cytokinesis.

By post-irradiation day 5, the frequency of bi and multinucleate cells reached about 95%, of which 20% were displaying endoapoptosis at a given time. The alterations in the kinetics of DNA synthesis due to irradiation was consistent with a transient radiation-induced arrest of cells in G1 (peeking at about 12 h after irradiation), which was soon followed by continuous DNA synthesis leading to endomitosis and endoreduplication through several rounds of DNA synthesis without cytokinesis. By post-irradiation day 5, some giant multi nucleate endoapoptotic cells were undergoing cytokinesis, giving rise to small mononucleate cells. These small mononucleate cells actively synthesized DNA and proliferated to form colonies of small mononucleate cells within a few weeks. The giant multinucleate cells were not active in synthesizing DNA by day 8–10, but remained alive for up to four weeks, the duration of observation.

The clonogenicity of multinucleate endoapoptotic giant cells was also confirmed by plating HeLa cells on post-irradiation day 4 on gridded petri plates and observing individual marked cells at 6–12 h intervals for up to 10 days. In addition, four days after irradiation, irradiated HeLa cells were plated on 10 cm petri plates at different cell concentrations and their colony forming ability confirmed (Table 4).

TABLE 3

HeLa cells showing BLDR (+BLDR) incorporation at different times after exposure to X-radiation (10 Gy). BiN, binucleate cells, MuN, multinucleate; MoN, mononucleate; PIH, post-irradiation hour; PID, post-irradiation day. At each time point, 300–500 cells were scored and the frequency of different categories of cells are expressed as percentage. (See also FIG. 2).

| Time after exposure to radiation | MuN cells | | | BiN cells | | | MoN cells | | |
|---|---|---|---|---|---|---|---|---|---|
| | +Bldr. | −Bldr. | Total | +Bldr. | −Bldr. | Total | +Bldr. | −Bldr. | Total |
| Unirradiated control | | | | | | | | | |
| Day 0 | 0.0 | 0.0 | 0.0 | 0.0 | 1.3 | 1.3 | 24.3 | 74.4 | 98.7 |
| Day 1 | 0.5 | 0.0 | 0.5 | 3.3 | 0.0 | 3.3 | 93.0 | 3.7 | 96.7 |
| Day 2 | 0.9 | 0.0 | 0.9 | 0.4 | 0.0 | 0.4 | 65.0 | 32.8 | 97.8 |
| Day 3 | 1.0 | 0.0 | 1.0 | 0.0 | 3.0 | 3.0 | 75.0 | 21.0 | 96.0 |
| Irradiated | | | | | | | | | |
| PIH 3 | 0.0 | 0.0 | 0.0 | 0.4 | 0.0 | 0.4 | 52.6 | 47.0 | 99.6 |
| PIH 6 | 0.0 | 0.0 | 0.0 | 0.4 | 0.6 | 1.0 | 45.6 | 53.4 | 99.0 |
| PIH 12 | 0.0 | 0.0 | 0.0 | 0.0 | 0.3 | 0.3 | 35.6 | 64.1 | 99.1 |
| PID 1 | 3.0 | 0.5 | 3.5 | 6.2 | 10.1 | 16.3 | 8.9 | 71.4 | 80.3 |
| PID 2 | 4.6 | 6.9 | 11.5 | 14.0 | 10.7 | 24.7 | 19.9 | 44.0 | 63.9 |
| PD 3 | 33.9 | 37.7 | 71.6 | 11.3 | 10.7 | 22.0 | 1.3 | 5.2 | 6.5 |
| PD 5 | 17.3 | 59.5 | 76.8 | 4.3 | 12.6 | 16.9 | 0.8 | 5.5 | 6.3 |
| PD 7 | 66.0 | 9.5 | 75.5 | 12.5 | 5.5 | 18.0 | 0.0 | 5.5 | 5.5 |
| PD 10 | 9.0 | 67.0 | 76.0 | 0.0 | 16.8 | 16.8 | 0.0 | 8.0 | 8.0 |

TABLE 4

Colony assay of X-irradiated HeLa cells (0, 5, 10, and 15 Gy)
after four weeks of growth at different cell densities.
Cells were plated four days after irradiation, at which time
95% of the cells are multinucleate giant cells with after
irradiation with 10 Gy units of X-radiation. Colonies of diameter
above 1 mm were (about 100 cells) were counted as viable colonies.
Since HeLa cells often detached and floated away during the mitotic
phase, these are bound to grow as satellite colonies, giving rise
to more colonies than the original number of cells seeded per plate.
In spite of that, the irradiated cells showed lower number of
colonies with increasing dose of irradiation.

| Cells seeded/plate | X-irradiation Dose (Gy) | | | |
|---|---|---|---|---|
| | 0 | 5 | 10 | 15 |
| 250 | 321 | 189 | 73 | 19 |
| 500 | 678 | 269 | 111 | 26 |
| 1000 | 1568 | 623 | 199 | 32 |

The colonies isolated from this assay were grown by subculturing up to 3 months (duration of observation). When Hela cells derived from the post-irradiation colonies were subjected to irradiation, they also formed multinucleate endoapoptotic giant cells as above, which survived to form colonies of mononucleate cells.

Endoapoptosis: self-destruction of the nascent daughter cell before birth

The studies reported herein with TdT labeling, acidine orange and DAPI staining, and transmission electron microscopy indicated that in multinucleate cells found in preneoplastic and neoplastic cells, one or more nascent mini cells (nucleus along with associated cytoplasm) were eliminated by endoapoptosis, a process that involves events similar to apoptosis including DNA fragmentation, chromatin marginization and condensation, and fragmentation of the endoapoptotic body. DNA fragmentation was initiated in an otherwise normal looking nucleus (no visible chromatin condensation or fragmentation of the nucleus). Hydrogen peroxide-induced apoptosis of A10 cells indicated that the temporal sequence of nuclear post-mortem events in classical apoptosis and endoapoptosis were very similar.

Endoapoptotic changes were seen in a nearly intact nucleus, which made it unlikely that endoapoptosis was due to phagocytosis of an apoptotic body, since the nucleus in the apoptotic cell would have undergone condensation and fragmentation before being phagocytosed by a neighboring cell.

It was observed that often both nuclei in a cell underwent DNA fragmentation, which eventually resulted in the classic apoptosis, which could have been due to the cell phagocytosing two intact nuclei that were being dismantled. Similarly, the high frequency of endoapoptosis in high cell density conditions were not due to phagocytosis of an apoptotic fragment for the following reasons: (a) one could recognize very early stages of DNA fragmentation in an otherwise intact nucleus, which was unlikely to have been phagocytosed; (b) the fine structure of asymmetric intracellular cytokinesis showing vesicles coalescing to form plasma membrane indicated that compartmentalization occurred intracellularly and not by phagocytosis of an extracellular apoptotic fragment; (c) the cells before and after formation of the transformed foci had more than one endoapoptotic nuclei. Phagocytosis of an apoptotic body could not preferentially occur only in the transformed foci, which also contained several cells in the very early stages of DNA fragmentation and chromatin condensation; (d) the diploid primary cultures maintained under similar conditions did not show any increase in endoapoptotic bodies or phagocytosed dead cells; (e) in irradiated HeLa cells, endoapoptosis was preceded by active DNA synthesis and multinucleation, which indicated a prerequirement of multinucleate cell formation for endoapoptosis to occur; (f) phagocytosis is an active process involving actin-myosin containing microfilaments [29]; however, incubation of A10 cells for 48 h in cytochalasin B (2 $\mu$g/ml in culture medium) that breaks down microfilaments did not reduce the frequency of endoapoptotic bodies.

Anatomy of endoapoptosis

The fragmentation of DNA during endoapoptosis as indicated by TdT end labeling occurred very early in the process, before the process of chromatin condensation was microscopically visible. This was followed by chromatin margination and condensation. Both light and transmission electron microscopy revealed that the endoapoptotic body included not only the nucleus, but also a small but varying amount of cytoplasm with vesicles and mitochondria. In addition, the dying nascent mini cell was compartmentalized by a process involving microfilaments from the living portion of the cytoplasm by asymmetric intracellular cytokinesis. Often the nuclear envelope in the dying mini cell disintegrated. The mini cell underwent shrinkage resulting in the separation of the plasma membranes of the mother cell and the dying mini daughter cell. The condensed chromatin was dismantled and was no more recognizable. The fibrillogranular material representing residual nuclear matrix also eventually disappeared, leaving a mini cell 'ghost' in the absence of fragmentation of the endoapoptotic body or several smaller 'ghosts' if the endoapoptotic body underwent fragmentation. Endoapoptosis shared several features with classic apoptosis such as DNA fragmentation, chromatic condensation and marginization, fragmentation of the (endo)apoptotic body, and dissolution of the nuclear envelope. Further, endoapoptosis represents premature post-karyokinetic death and disintegration of an unborn nascent cell resulting in abortive cell division that occurs within the mother cell that survives and reproduces, while apoptosis is a process that results in the death of an individual cell.

Cell cycle and endoapoptosis

Ionizing radiation induces chromosomal aberrations that can lead to cell death by apoptosis [28]. The results of the fusion experiments reported above with irradiated and non-irradiated cells (Table 2) indicated that the radiation-induced chromosomal damage and not the bi- or multi nucleate condition by itself were primarily responsible for the induction of endoapoptosis. Transmission electron microscopy revealed that the endoapoptotic body included a small amount of cytoplasm along with the defective nucleus, compartmentalized by a double membrane consisting of the plasma membrane of the mini cell (the inner membrane) and the plasma membrane of the viable cell. During the onset of metaphase, the nuclear membrane, endoplasmic reticulum and the membranes of the Golgi system are dismantled into smaller vesicles and are reorganized into membrane organelles during late telophase [27]. Given this sequence of events in bi or multinucleate endoapoptotic cells, endoapoptosis of the non-viable nucleus would have been initiated right after the completion of chromosomal segregation to the opposite poles of the spindle body and the formation of the nuclear membrane (karyokinesis) but before extensive reorganization of the endoplasmic reticulum and the Golgi system. The production of mini cell with a very small amount of cytoplasm as compared to the rest of the cell indicated that the mini-daughter cell was a result of asymmetric cytokinesis, which is commonly found in embryonic cells [27]. However, the uniqueness in the case of endoapoptosis was that asymmetric cytokinesis occurred intracellularly and resulted in the encapsulation of the dying daughter cell within the cytoplasm of the surviving daughter cell. Therefore, the preparation for the execution of endoapoptosis was probably initiated in late telophase and the nascent mini cell self-destructed before it was born. Depending on how early after telophase the process of endoapoptosis is initiated, the abortive daughter cell may include small but varying amount of cytoplasm including endoplasmic reticulum and associated vesicular structures. Thus, the elimination of non-viable mini daughter cells by post-mitotic intracellular apoptotic death or endoapoptosis resulted in partially abortive cell division and preservation of the major fraction of the cell from total cell death by compartmentalization of the dying mini cell with no net increase in cell number. One cell may display several endoapoptotic mini cells, indicating that the viable nucleus can repeatedly divide giving rise to one viable nucleus and one defective nucleus.

It was observed that the endoapoptotic mini-cell may or may not be fractionated during its demise. The rate of division and the rate and mode of endoapoptosis of the defective mini cell varied between different cell types. Thus, in A10 and ACHN cells several (up to 7 or 8) endoapoptotic mini cells were observed within one giant cell in various stages of disintegration. The fibrosarcoma derived HT1080 cells appeared to fragment and dismantle endoapoptotic mini-cells rapidly without accumulating them in the cytoplasm. But the metastasizing neuroblastoma derived HTB11 cells rapidly purged the endoapoptotic mini-cells by exocytosis (still birth), a process which may lead to phagocytosis of the dead mini-cells by neighboring cells, as in the case of classic apoptosis.

Figure 3:
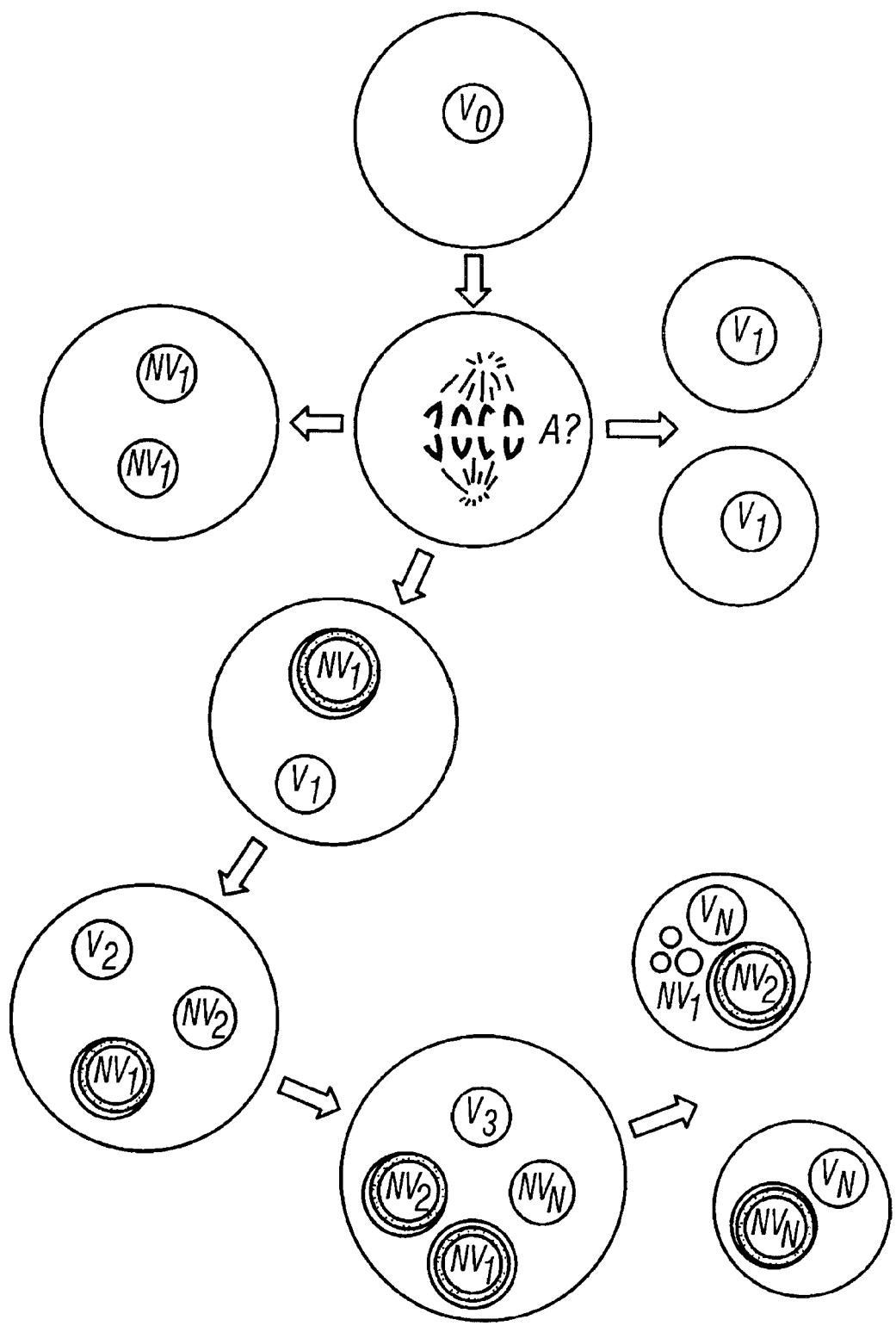
FIG. 3—Schematic representation of events in preneoplastic cells during cell density-induced genetic instability, repeated karyokinesis and asymmetric intracellular cytokinesis followed by endoapoptosis and its effect on cell proliferation. $V_{1-N}$ and $NV_{1-N}$ represent the successive generations of viable and nonviable nuclei.

It will be understood that, as diagrammed in FIG. 3, the process of karyokinesis was followed by asymmetric intracellular cytokinesis, and that endoapoptosis did not result in an increase in cell number until one viable nucleus gives rise to two viable nuclei. Although not restricted to the following explanation, the probable events during repeated cycles of endoapoptosis is diagrammatically shown in FIG. 3, which schematically represents events in preneoplastic cells during cell density-induced genetic instability, repeated karyokinesis and asymmetric intracellular cytokinesis followed by endoapoptosis and its effect on cell proliferation. $V_{1-N}$ and $NV_{1-N}$ represent the successive generations of viable and nonviable nuclei. Depending on the presence of normal or lethal chromosomal segregation during anaphase, the outcome of mitosis of a viable nucleus ($V_0$ nucleus) could be any three of the following:

a. formation of two viable nuclei (two $V_1$ nuclei) followed by cytokinesis resulting in two viable cells;
   b. formation of two non-viable nuclei (two $NV_1$ nuclei) that will result in apoptosis of the binucleate cell; alternatively cytokinesis might follow and both daughter cells might apoptose (not shown).
   c. formation of one viable nucleus ($V_1$) and one nonviable nucleus ($NV_1$); this shall lead to abortive cell division by endoapoptosis resulting in demise of $NV_1$ nucleus, while the $V_1$ is viable and capable of mitosis. (An alternative and probably more normal outcome not shown here would be the nuclear division forming $V_1$ and $NV_1$, followed by cytokinesis and the demise by apoptosis of the cell containing the $NV_1$ nucleus).

When $V_1$ enters mitosis all the above outcomes are possible. When the $V_1$ nucleus divides to yield one viable ($V_2$) and one non-viable nucleus ($NV_2$), the cell would have now two endoapoptotic nuclei, probably in progressive stages of disintegration. Continuation of this process would yield cells with multiple endoapoptotic bodies with one or more viable nuclei. This would favor formation of giant cells. There shall not be a net increase in cell number, until the division of the viable nucleus ($V_3$) gives rise to two viable nuclei ($V_N$), and is followed by cytokinesis. Different tumor cells seem to dispose the dead mini cells by slightly different mechanisms. Some tend to accumulate endoapoptotic body in the cytoplasm (A10 and HeLa cells); some disintegrate the endoapoptotic body faster without accumulating them in the cytoplasm (HT1080, NIH3T3) or exocytose the dead mini cells rapidly (HTB11 cells) (see text for details). In the multinucleate endoapoptotic giant cells formed after irradiation, similar events may occur, except that the genetic instability is induced by irradiation; similar events may be induced by other genotoxic agents.

Induction of endoapoptosis by cell density

It was observed herein that prolonged maintenance of preneoplastic cells and some neoplastic cells in confluence dramatically increased the frequency of endoapoptosis.

By way of hypothesis but not limitation, it appeared that in aneuploid cells (A10 and ACHN) endoapoptosis was caused by karyotype (genotype) instability, resulting in the elimination of the defective daughter cells. In irradiated tumor cells, DNA strand breaks initiate multinucleate endoapoptotic cells. Then, it follows that in preneoplastic cells such as NIH3T3 and A10 cells, prolonged cell—cell contact under confluence may induce increased karyotype (genotype) instability and therefore, endoapoptosis.

It was observed that endoapoptosis occurred in groups of cells under high cell density and that transformed foci derived from such cells. During the period of prolonged maintenance at high cell density there appeared to be no net increase in cell number, and eventually transformed cells arose in these foci via endoapoptosis. High cell density which favored transformed focus formation in the preneoplastic NIH3T3 cells, as reported above, may be related to hyperplasia preceding tumorigenesis in vivo [41, 42] and endoapoptosis might select for cells with genotypes that favor overgrowth and increased saturation density. Accordingly, it appeared from the results obtained herein that cell density-induced genomic instability and elimination of non-viable cells by endoapoptosis, followed by clonal expansion and selection of cells with higher survival value occurred several times during the progression of preneoplastic cells to neoplastic through malignant state. The neoplastic cells gave rise to 'further transformed' cells, which drove the surviving population toward higher degree of malignancy, while other cells were selected against. The observation herein of cell density dependent 'further transformation' of ACHN tumor cells represented an event in the multi-step progression of carcinogenesis, which was detected by determining the frequency of endoapoptosis in the ACHN tumor cells using the method of the invention.

Multinucleate endoapoptotic cells (2–3%) in phase III diploid fibroblasts persisted for a long time (several months), while in established cell lines NIH3T3 and A10, formation of endoapoptotic cells followed by transformed foci formation occurred in about 10 or 4 weeks, respectively, after attainment of confluence. In tumor derived cell line ACHN, cell density dependent induction of endoapoptosis and 'further transformed' foci formation was very rapid, of the order of 3–5 days. In HTB11, HT1080 and BT20 cells, endoapoptosis was observed even under low density conditions. Accordingly, it appeared that there was a progressive loss of density dependence for the induction of genomic instability and endoapoptosis, through the progression of the evolving neoplasia. The presence of nuclear ghosts (2–3%) in late passage diploid fibroblasts indicates that abortive cell division by endoapoptosis plays a role also in the parasexual cycle of polyploidization/rediploidization observed during the emergence of immortal rodent cell lines [44, 45].

Induction of multinucleate endoapoptotic cells by ionizing radiation

It was observed herein that exposure of tumor cell lines to ionizing radiation produced multinucleate endoapoptotic cells. Application of genotoxic agents including irradiation to cancer patients relies on the ability of these agents to induce cell death by apoptosis in tumor cells. Irradiation of tumor cells leads to cell death by apoptosis [46, 47] and leads to reduction in tumor size [48]. However, the failure of these treatment modalities to eliminate all tumor cells is caused in part by tumor cells being resistant to induction of apoptosis by these agents [9]. Resistance to genotoxic agents in tumor cells may be caused by different mechanisms including DNA repair systems (radiation resistance), multi drug resistance and detoxification mechanisms [49–51].

Formation of potentially clonogenic multinucleate endoapoptotic giant cells after irradiation observed herein is a novel mode of surviving the genotoxic damage in cancer cells. Accordingly, a method of the invention for determining the effectiveness of anti-tumor therapy (e.g. genotoxic agents such as radiation or chemicals) determines the frequency of such endoapoptotic cells in a tumor obtained from a patient periodically before, during, or after anti-tumor therapy. Irradiated cells synthesized DNA continuously and became multi nucleate in the absence of mitotic figures, which indicated that multinucleate giant cells were formed by endomitosis/endoreduplication. This contrasted to regular mitosis observed in cells undergoing density-dependent endoapoptosis. The non-viable nuclei in these multinucleate giant cells committed suicide by endoapoptosis, while the viable nuclei eventually separated from the multi nucleate giant cells by cytokinesis giving rise to small rapidly growing clones of cells.

In the studies reported herein, the frequency of occurrence of endoapoptosis in preneoplastic cells was one of the earliest and critical events that gave rise to clonal growth of rapidly dividing cells, which broke the barrier of limited division potential in primary cultures. Bi and multinucleate cells, commonly found in preneoplastic and neoplastic cell lines, were capable of selectively eliminating one or more defective daughter cells before birth by the endoapoptotic process discovered herein that shares many features with the classical apoptosis and also has some dissimilarities as listed in Table 5.

TABLE 5

Comparison of Events During Apoptosis and Endoapoptosis

| APOPTOSIS | ENDOAPOPTOSIS |
|---|---|
| SIMILARITIES: | |
| Constitutive gene expression | |
| Active Process | |
| DNA fragmentation | |
| Chromatic condensation and marginization | |
| Acidification of the nucleus | |
| Cell shrinkage & fragmentation | |
| Dissolution of nuclear envelope | |
| Formation of apoptotic/endoapoptotic bodies | |
| No inflammatory response | |
| Repair DNA synthesis | |
| Induced by genotoxic agents | |

TABLE 5-continued

Comparison of Events During Apoptosis and Endoapoptosis

| APOPTOSIS | ENDOAPOPTOSIS |
|---|---|
| DISSIMILARITIES: | |
| Occurs in normal or neoplastic cells | Occurs in preneoplastic and neoplastic cells |
| Cell density independent | Cell density dependent |
| Individual cells affected | Groups of cells may be affected |
| Induction by external and internal stimuli | Induction by internal stimuli |
| Cell cycle dependent [5] or independent [4] | Cell cycle dependent |
| Total cell death | No total cell death |
| Compartmentalization not required | Compartmentalization required |
| Heterophagocytosis | Hetero- or Autophagocytosis |

As observed herein, endoapoptosis was distinct from classical apoptosis in that there was no total cell death and the cell survived with the viable nucleus that was clonogenic. Unlike the classic apoptosis, which occurred in individual cells, endoapoptosis was induced by high cell density and occurred in groups of cells. In preneoplastic cells, endoapoptosis conserved living matter, provided an escape from contact inhibition of cell division, and favored survival of viable nuclei that proliferated to form transformed foci. Since chromosomes segregate randomly to two daughter nuclei during mitosis, this provided genetic variation in the progeny for the process of natural selection to act upon. Therefore, endoapoptosis played a role in favoring genomic stability by prematurely eliminating the non-viable daughter cells both in the preneoplastic and neoplastic cells or after exposure to genotoxic agents such as ionizing radiation.

Selection of viable nuclei via endoapoptosis occurred repeatedly during the discontinuous but discrete multistep evolution of the neoplastic cell. Since the presence of one endoapoptotic nucleus in a bi or multinucleate cell did not mean the cell was dead, determining the frequency of endoapoptosis in a sample of tumor tissue or a sample of abnormal tissue from a subject indicates the degree of risk that that subject has of developing tumor progression. The frequency of endoapoptosis has a bearing on the interpretation of the histochemical studies in tumor tissues that aim at predicting the prognosis based on the apoptotic index arrived at using paraffin sections of tumor tissues [62–64], in which it would be difficult to distinguish between mono and multinucleate cells. As the high frequency of classical apoptosis (total cell death) is an indication of favorable prognosis, high frequency of endoapoptosis may be an indication of the opposite, i.e. a prognosis of tumor progression, neoplasia, or malignancy.

EXAMPLE 2

Clinical and Clinical Research Protocols

In practice, the protocols of the present invention for determining the frequency of endoapoptosis in either a sample of normal or tumor tissue, or single cell suspensions of tumor biopsies, or single cell suspension of tumor derived cell cultures, or even of single cell suspensions derived from normal tissues or normal cell cultures are based, in part, on standard techniques well known by practitioners in the art for obtaining and histopathologically examining solid tissues, hematogenous tumor, or single cell suspensions thereof for diagnosis or prognosis and for monitoring the effects of anti-tumor therapy (70–75).

It is a matter of routine skill to adapt these techniques known in the art to the methods of the present invention to achieve the following:

Detecting if a subject with tumor cells is at increased risk of developing tumor progression;

Detecting malignancy of tumor tissue

Monitoring the status of a tumor in a patient over time

Determining the clinical stage of a cancer

Screening one or more tissues from a patient for the presence of malignant cells Screening for the presence of metastatic disease in a biological sample Screening for the presence of genomic instability in a biological sample Screening an agent for its effect on tumor progression.

Typically, a tissue biopsy is prepared for light microscopy as described above. Single cell suspensions of tumor biopsies or of tumor derived cell cultures are layered on glass cover slips, and examined microscopically to determine the frequency of endoapoptosis. Alternatively, single cell suspensions of tumor biopsies or of tumor derived cell cultures are subjected to flow cytometry. Accordingly, either light microscopy or flow cytometry are used in the method of the invention to quantitate the frequency of endoapoptotic cells, apoptotic cells, and cell cycle analysis. A high frequency of endoapoptosis in an otherwise benign looking tumor growth indicates an increased risk for tumor progression into malignant state. A high frequency of endoapoptosis accompanied by a high frequency of cycling cells indicates malignancy. Based on tumor models with known frequency of endoapoptosis over a given time interval, the methods of the invention are achieved for monitoring status of a tumor from a subject over time or for determining the clinical stage of a cancer. One or more tissues from the same subject can be screened similarly for the presence of malignant cells.

Metastatic cells (HTB11 human fibrosarcoma) in the studies reported herein displayed rapid purging of endoapoptotic cells. This purging is an indicator for a highly metastatic tumor. Screening for the presence of purged endoapoptotic cells requires cells to be cultured for at least 1–2 days in vitro.

Determining the frequency of endoapoptosis is also a screen for genomic instability in a biological sample of tissue. Since genomic instability is known to increase as a tumor progresses toward malignancy, frequency of endoapoptosis would be a measure of genomic instability, and, a measure of the stage of tumor progression.

EXAMPLE 3

Kit for Cancer Screening

The invention further provides a kit for determining the frequency of endoapoptosis in a sample of tissue from a subject. Several versions of the kit are provided. In one embodiment, for determining the frequency of endoapoptosis by light microscopy, the kit provides well known nuclear staining reagents (e.g. Giemsa or fluorescent dyes) known in the art for light microscopic examination of subcelluar anatomy, in particular the nucleus and chromosomes. By way of example but not limitation, such components include acridine orange, DAPI, reagents required for in-situ end labeling of DNA with 5-bromodeoxyuridine by terminal deoxytransferae, and the FITC conjugated anti-5-bromodeoxyuridine.

The invention provides an embodiment of a kit for quantitating endopoptosis by flow cytometry. By way of example, but not limitation, the kit includes propidium iodide, Hoescht 33342, 5-bromodeoxyuridine, terminal deoxytransferase, and the FITC-conjugated anti-5-bromodeoxyuridine, or FITC-labelled Annexin V.

The kit of the invention may include other reagents for distinguishing apoptosis from endoapoptosis, such as Cu/Zn superoxide dismutase for use in an ELISA assay, or monoclonal antibodies specific for certain cell surface markers of apoptosis.

Either version of the kit includes instructions for scoring the frequency of endoapoptosis of malignancy in tumorigenic cell lines in vitro (for research purposes) and tumor biopsies for clinical applications. Also included is a standard histogram showing the increase in the frequency of endoapoptosis through tumor progression from normal to malignant status using a model system well known in the art. As reference material for the light microscopy kit, model slides or color photographs of various forms of endoapoptosis are provided, as well as a descriptive pamphlet of endoapoptosis, the various fates of the endoapoptotic in different cancer cells, and a model describing endoapoptosis as it results from genomic-instability-induced defective cell division.

EXAMPLE 4

Screening Agents for Anti-Tumor Effects

In another aspect, the invention provides a method for screening an agent, such as a chemical agent, for its effect on tumor progression, and in particular, for the agent's anti-tumor effects, which would be its ability to interfere with tumor progression.

The method comprises a first step of providing a sample of tissue, either in the form of a biopsy mass or single cell suspensions thereof. In one aspect, the method determines the anti-tumor effects of the agent on tissue which it is known will progress toward malignancy at a known rate. The sample of tissue is exposed to the agent for a sufficient period of time and under conditions which allow a determination of the tissues progress towards neoplasia or malignancy, as determined by a method of the invention which determines the endoapoptotic frequency in the tissue.

After exposure to the agent, i.e. post exposure, the frequency of endoapoptosis in the tissue is determined and compared with the frequency of endoapoptosis for either normal tissue or for comparable tissue which as not been exposed to the agent. From measuring the endoapoptotic frequency in the exposed tissue or cells, the method thereby determines the effect of the agent on the emergence of a post exposure population of tumor cells, with a decrease in endoapoptotic frequency being an indication of the agent's anti-tumor effects.

The invention also provides a method for screening a putative anti-tumor agent for anti-tumor effects on a sample of normal tissue. This method involves providing a sample of normal tissue, which is then exposed to a genotoxic agent for a sufficient period of time to induce tumor progression in the normal tissue. The induced normal tissue is then exposed to the putative anti-tumor agent for an interval of time. The frequencies of endoapoptosis in the sample of tissue is determined over the interval of time. One then compares the frequencies, with a maintenance or decrease in frequency of endoapoptosis relative to unexposed tissue being an indication of the agent's anti-tumor effect.

It is intended that all matter contained in the above description or shown in the accompanying drawings shall be interpreted in an illustrative and not limiting sense.

Bibliography

1. Wyllie, A. H., J. F. R. Kerr, and A. R. Currie. (1980) Int. Rev. Cytol. 68:251–270.
2. Arends, M. J., and A. H. Wyllie. (1991) Int. Rev. Exp. Pathol. 32: 223–254.
3. Ellis, R. E., J. Yuan, and H. R. Horvitz. (1991). Annu. Rev. Cell Biol. 7: 663–698.
4. Raff, M. C. (1992) Nature 356: 397–400.
5. Meikrantz, W., and Schlegel, R. (1995) J Cell Biochem 58:160–174.
6. White, E. (1996). Genes Develop. 10, 1–15.
7. Hengartner, M. O., and H. R. Horvitz. (1994) Curr. Opin. Genet. Dev. 4:581–586.
8. Korsmeyer, S. J. (1995) Trends. Genet. 11: 101–105.
9. Fisher, D. E. (1994) Cell 78:539–542.
10. Yuan, J., S. Shaham, S. Ledoux, H. M. Ellis, and H. R. Horvitz, H. R. (1993) Cell 75:641–652.
11. Tewari, M., L. T. Quan, K. O'Rourke, S. Desnoyers, Z. Zeng, D. R. Beidler, G. G. Parer, G. S. Salvesen, and V. M. Dixit, V. M. (1995) Cell 81: 801–809.
12. Martin, S. J., and D. R. Green, D. R. (1995) Cell 82: 349–352.
13. Jacobson, M. D., J. F. Burne, and M. C. Raff. (1994) The EMBO J. 13: 1899–1910.
14. Schulze-Osthoff, K., H. Walczak, W. Droge, and P. H. Krammer. (1994) J. Cell Biol. 127: 15–20.
15. Nakajimua, H., P. Golstein, and P. A. Henkart. (1995) J. Exp. Med. 181: 1905–1909.
16. Caelles, C., A. Helmberg, and M. Karin. (1994) Nature 370: 220–223.
17. Rajaraman, R, Faulkner, G., Sinha, S., and Gatchalian, F. (1995) Mol. Biol. Cell 6: Suppl. 342a.
18. Gorczyca, W., J. Gong, and Darzynkiewics, Z. (1993) Cancer Res. 53: 1954–1951.
19. Duke, R. C., and J. J. Cohen. (1992) In *Current Protocols in Immunology*. Ed. J. E. Coligan, A. M. Kruisbeck, D. H. Margulies, E. M. Sheuch, and W. Strober. USA: John Wiley & Sons, Inc. 1: 3.17–3.18.
20. Darzynkiewicz, Z. (1994) In: Cell Biology. A Laboratory Handbook. Ed. Celis, JE. Academic Press, London-New York. Vol 1.261–271.
21. Magaud, J. P., I. Sargent, P. J. Clarke, M. Ffrench, R. Rimokj, and D. Y. Mason. (1989) J. Histochem. Cytochem. 37: 1517–1527.
22. McGahon, A. J., Martin, S. J., Bissonette, R. P., Mahboubi A., Shi, Y., Mogil, R. J., Nishioka, W. K., and Green, D. R. (1995) Methods Cell Biol. 46: 153–185.
23. Hockenbery, D. M., Z. N. Oltvai X. -M. Yin, C. L. Milliman, and S. J. Korsmeyer. (1993) Cell 75, 641–652.
24. Gottlieb, R. A, J. Nordberg, E. Skowronski, and B. M. Babior. (1996) Proc Natl Acad Sci USA 93:654–658.
25. Kim, W. H., Schnaper, H. W., Nomizu, M., Yamada, Y., and Kleinman, H. K. (1994) Cancer Res. 54: 5005–5010.
26. Maeda, S., H. Kimura, N. Koga, K. H. Lin, and T. Saito. (1993) Biochem. Biophys. Res. Commun. 195: 270–275.
27. Warren, G. (1993). Annu. Rev. Biochem. 323–348.
28. Berges, R. R., Y. Furuya, L. Remington, H. F. English, T. Jacks, and J. T. Isaacs. (1993) Proc. Natal. Acad.. Sci. USA 90: 8910–8914.
29. Watanabe, s., Hirose, M., Ueno, t., Kominami, e., and Namihisa, T. (1990). Liver 10:249–54.
30. Dewey, W. C., C. C. Ling, R. E. Meyn (1995) Int. J. Radiat. Oncol. Biol. Phys. 33: 781–796.
31. Zen, K., J. Masuda, T. Sasaguri C. Kosaka, and J. Ogata, J. (1994) Exp. Cell Res. 215:172–179.
32. Cizmeci-Smith, G., R. C. Stahl, L. J. Showalter, and D. J. Carey. (1993) J Biol. Chem. 268: 18740–18747.
33. Vitale, M., A. Casamassima, M. Illario, V. Bassi, G. Fenzi, and G. Ross. (1995) Exp. Cell Res. 220:124–129.
34. Bost, L. M., and L. M. Hjelmeland. (1993) Growth Factors 9:195–203.
35. Jin, P., K. Farmer, N. R. Ringertz, and T. Sejersen. (1993) Differentiation 54: 47–54.
36. Wu, K. F., Q. Rao, G. G. Zheng, Y. Q. Geng, M. Li, J. Kong, Y. H. Song, H. G. Ying, and B. D. Chen. (1994) Leukocyte Res. 18:843–849.
37. Van den Ent, F. M., A. J. van Wijnen, T. J. Last, R. Bortell, J. L. Stein, J. B. Lian, and G. S. Stein. (1993) Cancer Res. 53:2399–2409.
38. Poumay, Y., and M. R. Pittelkow. (1995) J. Invest. Dermatol. 104: 271–276.
39. Mathieu, C., Jozan, S., Mazars, P., Come, M. G., Moisand, A., and Valette, A. (1995) Exp. Cell Res. 216: 13–20.
40. Deffie, A., M. Hao, B. M. D-O. Luna, D. L. Hulboy, and G. Lozano. (1995) Mol Cell Biol 153926–3933.
41. Rubin, H., A. Yao, and M. Chow. (1995)Proc. Natl. Acad. Sci. USA 92:4843–4847.
42. Rubin, H., A. Yao, and M. Chow. (1995) Proc. Natl. Acad. Sci. USA 92: 7734–7738.
43. Shin, D. M., N. Voravud, J. Y. Ro, J. S. Lee, W. K. Hong, and W. N. Hittelman. (1993) J. Natl. Cancer Inst. 85:971–978.
44. Micale, M. A, D. W. Visscher, S. E. Gulino, and S. R. Wolman. (1994) Hum. Pathol. 25: 29–35.
45. Rothfels, K. H., E. B. Kupelwieser, and R. C. Parker. (1962) Canadian Cancer Conference 5: 191–223.
46. Littlefield, J. W. *Variation, Senescence, and Neoplasia in Cultured Somatic Cells.* Harvard University Press, Cambridge, Mass. and London, England (1976).
47. Radford, I. R., and T. Murphy. (1994) Int. J. Rad. Biol. 65: 229–239.
48. Radford, I. R., T. Murphy, J. M. Radley, and S. Ellis, S. (1994) Int. J. Rad. Biol. 65: 217–227.
49. Stephens, I. C., K. K. Ang, T. E. Schultheiss, L. Milas, and R. E. Meyn. (1991) Rad. Res. 127:308–316.
50. Carmichael, J., and I. D. Hickson. (1991) Int. J. Radiat. Oncol. Biol. Phys. 20:197–202.
51. Weichselbaum, R. R., M. A. Beckett, D. E. Hallahan, D. W. Kufe, and E. E. Vokes. (1992) Seminars in Oncol. 19:Suppl. 11, 14–20.
52. Maity, A., W. G. Mckenna, and R. J. Muschel. (1994) Radiotherap. Oncol. 31:1–13.
53. Sargent, L. M., Y. P. Dragan, N. Bahlub, J. E. Wiley, C. A. Sattler, P. Schroeder, G. L. Sattler, V. C. Jordan, and R. C. Pitot. (1994) Cancer Res. 54: 3357–3360.
54. Traganos, F., J. Gong, B. Ardelt, and Z. Darzynkiewicz. (1994) J Cell Physiol. 158:535–544.
55. Pathak, S., B. J. Dave, and S. Gagos. (1994) In Vivo 8: 843–850.
56. Tommerup, N., E. Mortensen, M. H. Nielson, R. D. Wegner, D. Schindler, and M. Mikkelsen. (1993) Hum. Genet. 92:339–346.
57. Matsumoto, K., and Ohta, T. (1992) Chromosoma 102:60–65.
58. Matsumoto, K., and T. Ohta. (1995) Mutat. Res. 326:93–98.
59. Quiet, C. A., R. R. Weichselbaum, and D. J. Grdina, D. J. (1991) Int. J. Radiat. Oncol. Biol. Phys. 20: 733–738.
60. Hayflick, L., and P. S. Moorehead. (1961) Exp. Cell Res. 25: 585–621.
61. Hartwell, L. H., and M. B. Kastan. (1994) Science 266: 1821–1828.
62. Pignolo, R. J., M. O. Rotenberg, and V. J. Cristofalo. (1994) In Vitro Cell Dev. Bio. Anim. 30A: 471–476.

63. Lipponen, P. K., and S. Aaltomaa. (1994) J. Pathol. 173:333–339.
64. Aihara, M., Scardino, P. T., Truong, L. d., Wheeler, T. M., Goad, J. R., Yang, G., and Thompson, T. C. (1995) Cancer 75: 522–529.
65. Lowe, S. W., Bodis, S., Bardeesy, N., McClatchey, A., Remington, L., Ruley, H. E., Fisher, D. E., Jacks, T., Pelletier, J., and Houseman, D. E. (1994) Cold Spring Harb. Symp. Quant. Biol. 59: 419–426.
66. Smith, M. I. et al., Curr. Opin. Oncol. (1995) 7:69–75
67. Kuozarides, T., Semin. Cancer Biol. (1995) 5:91–98
68. Schwartz J., et al. Radiat. Res. 146:139–143 (1996)
69. Cross, S. M., et al., Science 267:1353–1356 (1995)
70. DeVitta, V. T., Jr., et al. (eds) *Cancer Principles & Practice of Oncology,* 3rd ed, J. B. Lippincott Co,, Phil. (1989)
71. Borg, S. A., and Rosenthal, S., *Handbook of Cancer Diagnosis and Staging: A Clinical Atlas* John Wiley & Sons, NY (1984)
72. Wheater, P., et al., *Basic Histopathology, A color Atlas and test,* Churchill Livingstone, Edinburgh, London, NY.
73. Lemoine, N. R., *Cancer, A Molecular Approach,* Blackwell Scientific Publishers, Boston (1994).
74. University of Texas, MD Anderson Cancer Center. *Cancer Prevention and Detection in the Cancer Screening Clinic* (1988)
75. Herold, A. H., *Cancer Screening and Diagnosis,* Saunders, Phil. (1996)

What is claimed is:

1. A method of detecting malignancy of tumor tissue, comprising the steps of:
   (a) determining the frequency of endoapoptosis in a sample of tumor tissue;
   (b) comparing the frequency determined in step (a) with predetermined frequencies of endoapoptosis in reference standards of normal tissue, wherein the increased frequency of endoapoptosis in step (a) compared to step (b) indicates said tumor tissue is malignant.

2. A method of screening one or more tissues from a subject for the presence of malignant cells, the method comprising the steps of:
   (a) determining the frequency of endoapoptosis in a sample of said one or more tissues from said subject; and
   (b) comparing the frequency in step (a) with the frequency of endoapoptosis in a normal tissue reference standard, wherein the increased frequency of endoapoptosis in step (a) compared to step (b) indicates the presence of malignant cells in said one or more samples.

3. A method of diagnosing cancer in a subject, said method comprising the steps of:
   (a) determining the frequency of endoapoptosis in a sample of tumor tissue;
   (b) comparing the frequency determined in step (a) with predetermined frequencies of endoapoptosis in reference standards of normal tissue, wherein the increased frequency of endoapoptosis in step (a) compared to step (b) indicates a diagnosis of cancer in said subject.

4. A method of monitoring the frequency of malignant cells in one or more malignant tumor tissues from a subject over a time interval, said method comprising the step of determining the frequency of endoapoptosis in samples of said malignant tumor tissues, said samples obtained from said subject at one or more times before, during or after said subject receives anti-tumor therapy.

5. The method of claim 4 wherein said tumor is a solid tumor.

* * * * *